United States Patent [19]

Walker et al.

[11] 4,036,974
[45] July 19, 1977

[54] 1-{2'-[R'-THIO(OXY)]-3'-(R²-THIO(OXY)]-PROPYL}IMIDAZOLES

[75] Inventors: Keith A. M. Walker, Palo Alto; Michael Marx, Sunnyvale, both of Calif.

[73] Assignee: Syntex (U.S.A.) Inc., Palo Alto, Calif.

[21] Appl. No.: 664,840

[22] Filed: Mar. 8, 1976

Related U.S. Application Data

[63] Continuation-in-part of Ser. No. 599,611, July 28, 1975, abandoned.

[51] Int. Cl.² .................. A61K 31/415; C07D 233/60
[52] U.S. Cl. ...................... 424/273; 260/309;
   260/348 R; 260/609 F; 260/609 R
[58] Field of Search .............. 260/309; 424/273

[56] References Cited
U.S. PATENT DOCUMENTS

| | | | |
|---|---|---|---|
| 3,531,494 | 9/1970 | Adolphi et al. | 260/309 |
| 3,940,415 | 2/1976 | Buchel et al. | 260/309 |

*Primary Examiner*—Natalie Trousof

*Attorney, Agent, or Firm*—Alan M. Krubiner; William B. Walker

[57] ABSTRACT

Compounds of the formula

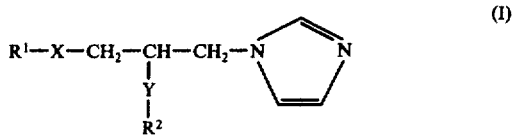

wherein $R^1$ and $R^2$ are independently alkyl or the group

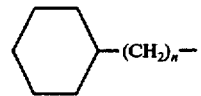

in which $n$ is 0 to 3; X and Y are independently oxygen or sulfur; and the antimicrobial acid addition salts thereof are useful as antifungal, antibacterial and antiprotozoal agents.

28 Claims, No Drawings

1-{2'-[R'-THIO(OXY)]-3'-(R²-THIO(OXY)]PROPYL-} IMIDAZOLES

RELATED APPLICATIONS

This case is a continuation-in-part of U.S. Ser. No. 599,611, filed July 28, 1975, now abandoned.

the present invention relates to novel chemical compounds which are derivatives of imidazole. More particularly, the present invention relates to compounds of the formula

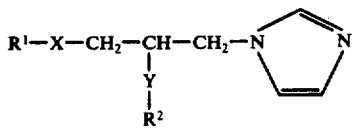

(I)

wherein $R^1$ and $R^2$ are independently alkyl or the group

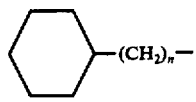

in which $n$ is 0 to 3; X and Y are independently oxygen or sulfur; and the antimicrobial acid addition salts thereof.

The term "alkyl" as used in the specification and appended claims refers to a saturated, unbranched or branched acyclic hydrocarbon group containing 1 to 12 carbon atoms, such as, methyl, ethyl, n-propyl, isopropyl, n-butyl, sec-butyl, isobutyl, tert-butyl, n-pentyl, n-hexyl, n-heptyl n-octyl, n-nonyl, n-decyl, n-undecyl, n-dodecyl and the like. The term "halo" refers to chloro, fluoro and bromo. The term "antimicrobial acid addition salts" refers to salts of the subject compounds which possess the desired activity and which are neither biologically nor otherwise undesirable. These salts are formed with inorganic acids such as hydrochloric acid, hydrobromic acid, sulfuric acid, nitric acid, phosphoric acid and the like; or organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid and the like.

All compounds of Formula (I) possess at least one chiral center, i.e., the carbon atom to which are attached the $R^1XCH_2$, $R^2Y$, H and

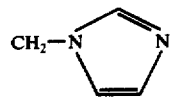

moieties. Accordingly, the compounds of the present invention may be prepared in either optically active form, or as a racemic mixture. Unless otherwise speicfied, the compounds described herein are all in the racemic form. However, the scope of the subject invention herein is not to be considered limited to the racemic form, but to encompass the individual optical isomers of the subject compounds.

If desired, racemic intermediates or final products prepared herein may be resolved into their optical antipodes by conventional resolution means known per se, for example, by the separation (e.g., fractional crystallization) of the diastereomeric salts formed by reaction of, e.g., racemic compounds of Formula (I) or the alcohol precursors of Formulas (1), (3) and (6) with an optically active acid, or by separation of the diastereomeric esters formed by the reaction of racemic alcohol intermediates with an optically active acid. Exemplary of such optically active acids are the optically active forms of camphor-10-sulfonic acid, α-bromo-camphor-π-sulfonic acid, camphoric acid, menthoxy-acetic acid, tartaric acid, malic acid, diacetyltartaric acid, pyrrolidone-5-carboxylic acid and the like. The separated pure diastereomeric salts or esters may the be cleaved byy standard means to afford the respective optical isomers of the compounds of Formula (I) or the precursor alcohols.

Alternatively, the subject compounds may be prepared in optically active form from optically active compounds of the formula

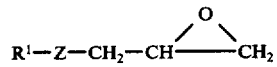

(15)

wherein Z is oxygen or sulfur.

The above compounds (15) are obtained from optically active forms of glycerol acetonide (2,2-dimethyl-1,3-dioxolane-4-methanol) by methods known in the art, e.g. J. Med. Chem. 1973, 16, pp. 168–169.

The subject compounds embraced by generic Formula (I) can be represented subgenerically as:

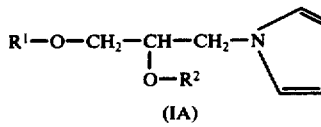 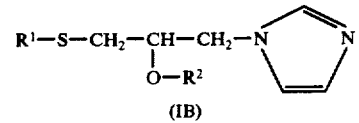

(IA) (IB)

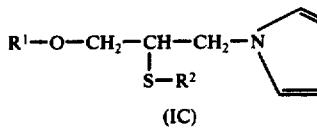 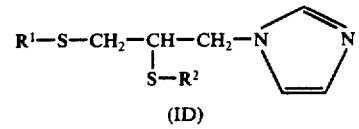

(IC) (ID)

wherein:

$R^1$ and $R^2$ are independently alkyl or the group

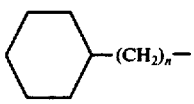

in which n is 0 to 3; and the acid addition salts thereof.

Preferred compounds embraced by subgeneric Formulas (IA), (IB), (IC), and (ID) are those wherein $R^1$ and $R^2$ are alkyl.

Particularly preferred compounds within the group described in the previous paragraph are:

1. Compounds of Formula (IA) wherein the $R^1$ and $R^2$ groups contain a total of 10 to 17 carbon atoms (preferably 11 to 15);
2. Compounds of Formulas (IB) and (IC) wherein the $R^1$ and $R^2$ groups contain a total of 8 to 15 carbon atoms (preferably 9 to 14); and
3. Compounds of Formula (ID) wherein the $R^1$ and $R^2$ groups contain a total of 7 to 14 carbon atoms (preferably 8 to 12).

Especially preferred compounds within the above defined groups 1 to 3 are those wherein $R^1$ and $R^2$ are straight chain alkyl.

The subject compounds of Formula (I) exhibit antifungal, antibacterial and antiprotozoal activity. For example, compounds of the present invention exhibit antifungal activity against human and animal pathogens such as

*Microsporum audouini,*
*Microsporum gypseum,*
*Microsporum gypseum-canis,*
*Epidermophyton floccosum,*
*Trichophyton mentagrophytes,*
*Trichophyton rubrum,*
*Trichophyton tonsurans,*
*Candida albicans* and
*Cryptococcus neoformans.*

The compounds of the present invention also exhibit antifungal activity against fungi of primarily agricultural importance such as

*Aspergillus flavus,*
*Cladosporium herbarum,*
*Fusarium graminearum,*
*Penicillium notatum,*
*Aspergillus niger,*
*Penicillium oxalicum,*
*Penicillium spinulosum* and
Pithomyces chartarum.

In addition, the compounds of the present invention exhibit antibacterial activity against human and animal pathogens, such as

*Staphylococcus aureus,*
*Streptococcus faecalis,*
*Corynebacterium acnes,*
*Erysipelothrix insidiosa,*
*Escherichia coli,*
*Proteus vulgaris,*
*Salmonella choleraesuis,*
*Pasteurella multocida* and
*Pseudomonas aeruginosa.*

Moreover, the compounds of the present invention exhibit antiprotozoal activity against protozoa such as *Trichomonas vaginalis*

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural and industrial use, which compositions comprise the subject compounds of Formula (I) in combination with a suitable carrier. A still further aspect of the present invention relates to methods of inhibiting the growth of fungi, bacteria and protozoa by applying to a host object containing, or subject to attack by, fungi, bacteria or protozoa an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, gels, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semisolid formulations there may be mentioned, for example, polyalkylene glycols, vaseline and other cream bases; for liquid formulations there may be mentioned, for example, water oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials. In pharmaceutical applications, the subject compounds and compositions may be administered to humans and animals by conventional methods, e.g., topically, orally, parenterally and the like. Parenteral administration includes intramuscular as well as subcutaneous and intravenous injection. Intravenous injection of imidazole derivatives for certain systemic conditions has been demonstrated to be effective (see for example, Drugs, 9, 419–420 (1975), which describes the intravenous administration of Miconazole, i.e., 1; -[2,4-dichloro-$\beta$-(2',4'-dichlorobenzyloxy)phenethyl]imidazole nitrate, to patients with systemic candidiasis).

Topical application is the preferred method of administration in pharmaceutical applications. For such treatment, an area having an existing fungal, bacterial or protozoal growth, or to be protected against attack by fungi, bacteria or protozoa may be treated with the subject compounds or compositions by, for example, dusting, sprinkling, spraying, rinsing, brushing, dipping, smearing, coating, impregnating and the like. Topical compositions containing the compounds of the present invention exhibit antifungal, antibacterial and antiprotozoal activity over a wide range of concentration, for example, from about 0.1 to 10.0% by weight of the composition.

The pharmaceutical compositions hereof typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, for systemic (e.g. oral or parenteral) administration it is expedient to administer the active ingredient in amounts of between about 1 and 100 mg./kg. body weight per day (preferably between about 5 and 50 mg./kg. body weight per day) distributed over seeveral applications (e.g. in 3 individual doses) in order to achieve effective results. For localized (e.g. topical) administration however, proportionately less of the active ingredient is required. The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner. In any event the compositions to be administered will contain a quantity of the subject compound in an amount effective for relief or prevention of the specific condition being treated.

In agricultural applications, the subject compounds may be applied directly to plants (e.g., seeds, foliage) or to soil. For example, compounds of the present invention may be applied to seeds alone or in admixture with a powdered solid carrier. Typical powdered carriers are the various mineral silicates, e.g., mica, talc, pyrophyllite and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agent, or the subject compounds can be applied as an aqueous spray optionally containing a surface-active dispersing agent and a powdered solid carrier. As a foilage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase their effectiveness, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

DETAILED DESCRIPTION

The present invention in a still further aspect is directed to methods for the preparation of the subject compounds of Formula (I).

Sequence 1

The following reaction sequence, directed to the preparation of compounds of Formulas (IA) and (IB), can be illustrated as follows:

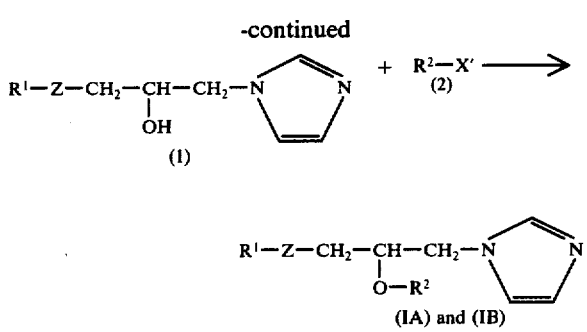

wherein $R^1$ and $R^2$ are as previously defined, z is oxygen or sulfur and X' is a conventional leaving group such as a halide (e.g. chloride or bromide) or a sulfonate ester (e.g. methane-sulfonate or p-toluenesulfonate).

In the above sequence, the imidazole derivatives of Formulas (IA) and (IB) are prepared by converting a hydroxy compound of Formula (1) to its metal salt by treatment with a strong base, such as sodium hydride and the like, and thereafter contacting the resulting metal salt with a compound of Formula (2). Preparation of the salt is effected in an organic solvent such as hexamethylphosphoramide, tetrahydrofuran, dimethylformamide and the like, at a temperature of 0° to 65° C. for a period of 30 minutes to 4 hours. Thereafter, reaction of the salt of (1) with a compound of Formula (2) is carried out in the same solvent at a temperature of 0° to 65° C. for a period of 1 to 24 hours.

Sequence 2

The following reaction sequence, directed to the preparation of compounds of Formula (IC), can be illustrated as follows:

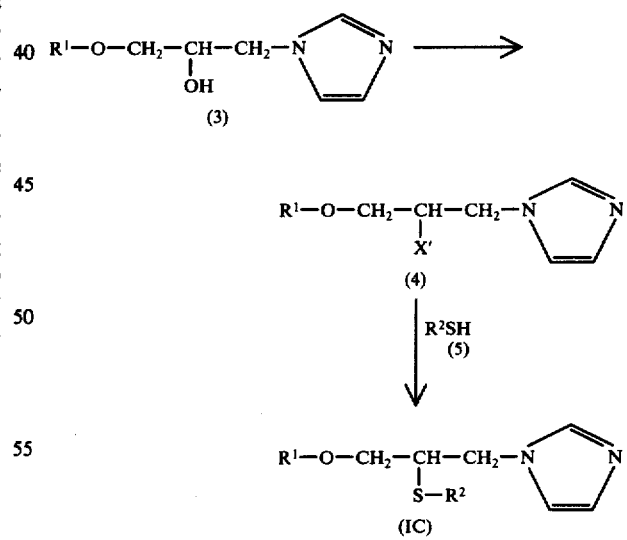

wherein $R^1$ and $R^2$ are as previously defined, and X' is a conventional leaving group such as a halide (e.g., chloride or bromide) or a sulfonate ester (e.g., methanesulfonate or p-toluenesulfonate).

In the above sequence, the imidazole derivatives of Formula (IC) are prepared from compounds of Formula (3) by a two-step sequence involving conversion of the hydroxy group to a suitable leaving group such as a halide (e.g., a chloride or bromide) or a sulfonate ester (e.g., methanesulfonate or p-toluenesulfonate) which is then reacted with a metal salt of a thiol of Formula (5).

The conversion of an alcohol of Formula (3) to a compound of Formula (4) is carried out by means well known in the art. For example; the alcohol may be halogenated using a halogenating agent such as thionyl chloride or thionyl bromide, either neat, or in an inert organic solvent such as dichloromethane or chloroform, at a temperature between about 0° to 80° C., preferably between about 20° and 80° C. The halogenation reaction may be carried out in the presence of a molar equivalent of a base (e.g., pyridine) if desired. Alternate halogenation procedures include, for example, the use of triphenylphosphine with either carbon tetrachloride, carbon tetrabromide or N-chloro (or N-bromo) succinimide. When utilizing thionyl chloride or thionyl bromide without the use of added base, the hydrochloride or hydrobromide salt of the corresponding halo compound is produced. This salt is preferably neutralized (e.g., with potassium carbonate) prior to its use in the thioalkylation step, however the salt may be used directly if excess thiol salt is utilized.

Sulfonate esters may be prepared by the standard procedure of treating the alcohol with an excess of, for example, methanesulfonyl chloride or p-toluenesulfonyl chloride, in the presence of a base, for example pyridine or triethylamine. This reaction is carried out at a temperature from about −20° to +50° C., preferably between about 0° and 20° C.

The thus obtained compounds of Formula (4) are then reacted with a metal salt, preferably an alkali metal salt such as the sodium or potassium salt of a thiol of Formula (5) to obtain the imidazole derivatives of Formula (IC). This reaction is carried out in an inert organic solvent such as tetrahydrofuran, ether, methanol and the like in the presence of a suitable base such as sodium hydride or sodium methoxide at a temperature of 20° to 67° C. for a period of 30 minutes to 72 hours.

Sequence 3

The following reaction sequence, directed to the preparation of compounds of Formula (ID), can be illustrated as follows:

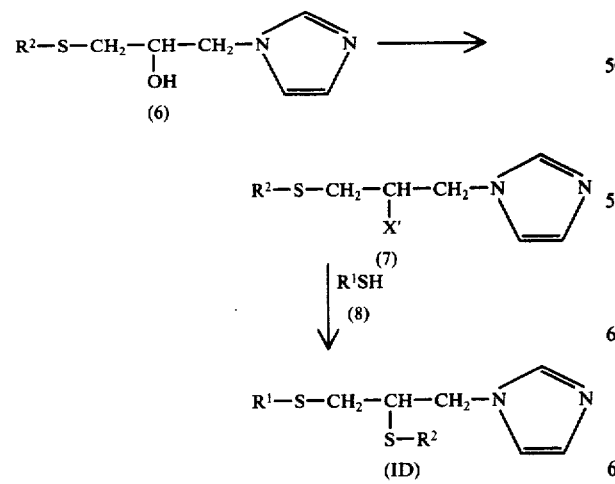

wherein $R^1$ and $R^2$ are as previously defined and X' is a conventional leaving group such as a halide (e.g., chloride or bromide) or a sulfonate ester (e.g., methanesulfonate or p-toluenesulfonate).

In the above sequence, compounds of Formula (7) are prepared in the same manner previously described for the preparation of compounds of Formula (4) in Sequence 2.

Thereafter the imidazole derivatives of Formula (ID) are prepared by reacting a compound of Formula (7) with a metal salt, preferably an alkali metal salt, of a thiol of Formula (8). This particular reaction proceeds via a cyclic intermediate with the net result being attachment of the entering $R^1$-S-moiety at the —CH$_2$- position and migration of the original $R^2$-S-moiety from this position to the —CH= position.

The reaction of compounds of Formula (7) with compounds of Formula (8) is carried out as previously described in the preparation of compounds of Formula (IC) in Sequence 2 (see paragraph 5).

Sequence 4

The following reaction sequence, directed to a second method for the preparation of compounds of Formula (IC), can be illustrated as follows:

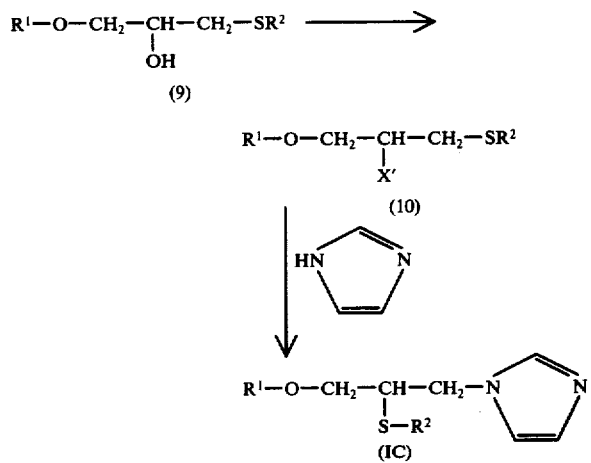

wherein $R^1$ and $R^2$ are as previously defined and X' is a conventional leaving group such as a halide (e.g., chloride or bromide) or a sulfonate ester (e.g., methanesulfonate or p-toluenesulfonate).

In the above sequence, compounds of Formula (10) are prepared in the same manner previously described for the preparation of compounds of Formula (4) in Sequence 2.

Thereafter, compounds of Formula (10) are reacted with imidazole in an organic solvent such as acetonitrile, dimethylformamide, and the like to obtain the imidazole derivatives of Formula (IC). This reaction is carried out at a temperature of 0° to 100° C. for a period of 1 to 24 hours.

Sequence 5

The following reaction sequence, directed to a second method for the preparation of certain compounds of Formula (ID), can be illustrated as follows:

-continued

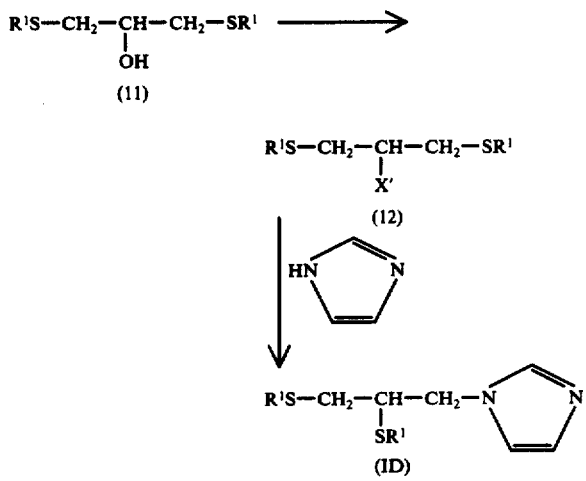

wherein $R^1$ is as previously defined and $X'$ is a conventional leaving group such as a halide (e.g., chloride or bromide) or a sulfonate ester (e.g., methanesulfonate or p-toluene-sulfonate).

In the above sequence, the compounds of Formula (12) are prepared in the same manner previously described for the preparation of compounds of Formula (4) in Sequence 2.

Thereafter, compounds of Formula (12) are reacted with imidazole in the manner previously described in Sequence 4 (paragraph 3) to obtain the imidazole derivatives of Formula (ID).

The subject compounds of the instant invention can be isolated as free bases, however, since many of the compounds in base form are oils or gums, it is more convenient to isolate and characterize the compounds as acid addition salts. These salts are prepared in the usual manner, i.e., by reaction of the base compound with a suitable inorganic or organic acid, described above. Salts formed with dibasic acids (e.g. oxalic acid) may contain one or two molecules of base per molecule of acid. All oxalates described herein contain one molecule of oxalic acid per molecule of imidazole base. If desired, the salts can be readily converted to the compounds in base form by treatment with alkali, such as potassium carbonate, sodium carbonate or sodium or potassium hydroxide.

The alcohols required as starting materials for preparation of the subject compounds of the instant invention are either available or can be obtained by known processes.

For example, the alcohols required in Sequences 1–3 can be prepared as follows:

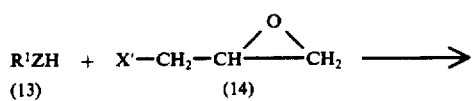

-continued

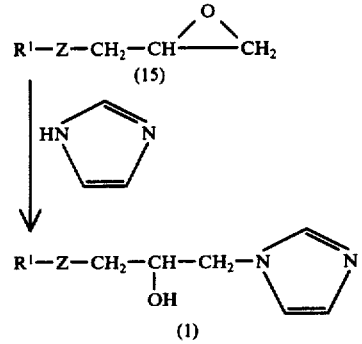

wherein $R^1$ is as previously defined, $X'$ is chloro or bromo and $Z$ is oxygen or sulfur.

In the above depicted sequence, the 2,3-epoxypropyl (thio)ethers of Formula (15) are prepared by reaction of a compound of Formula (13) with an epihalohydrin such as epichlorohydrin or epibromohydrin followed by reaction of the resulting 2,3-epoxypropyl (thio)ether with imidazole.

The reaction of compounds of Formula (13) with epihalohydrins is carried out in an inert organic solvent such as tetrahydrofuran, ether and the like in the presence of a suitable base such as sodium hydride at a temperature of 0° to 67° C. for a period of 30 minutes to 72 hours.

The thus obtained 2,3-epoxypropyl(thio)ethers of Formula (15) are then reacted with at least one molar equivalent of imidazole (preferably an excess) in an inert organic solvent such as acetonitrile, dimethylformamide and the like, at a temperature of 0° to 80° C. for a period of 1 to 72 hours to obtain the alcohols of Formula (1).

When $R^1$ is a small alkyl group such as methyl, ethyl etc., in alcohols of Formula (1), such alcohols tend to be relatively water soluble. In such cases, variations necessary in the reaction and work up procedures will be apparent to those skilled in the art. Such variations may include use of a low boiling organic solvent, non-aqueous work up, chromatographic separation, removal of excess imidazole at a later stage, etc.

The above discussion particularly applies to certain alcohols prepared in Preparations A and B on pages 19 to 20.

Alcohols required in Sequence 4 can be prepared as follows:

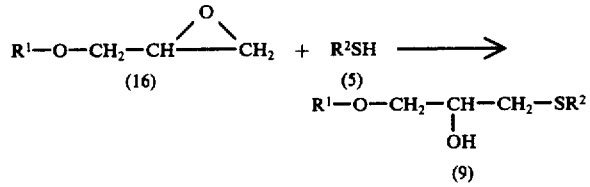

wherein $R^1$ and $R^2$ are as previously defined.

In the above depicted sequence, the alcohols of Formula (9) are prepared by reaction of a 2,3-epoxypropyl ether of Formula (16) with a thiol of Formula (5). This reaction is carried out in an inert solvent such as tetrahydrofuran, ether and the like in the presence of a suitable base such as sodium hydride at ambient temperature to reflux for a period of 30 minutes to 24 hours.

Alcohols required in Sequence 5 can be prepared as follows:

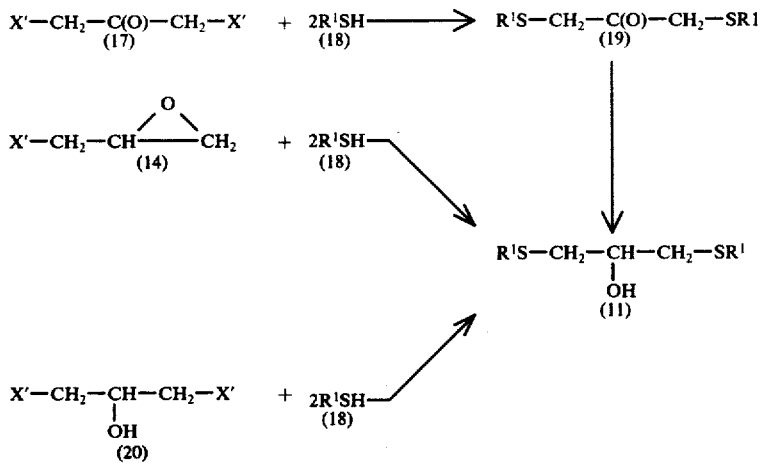

wherein $R^1$ is as previously described and $X'$ is chloro or bromo.

In the above depicted reaction sequences, the alcohols of Formula (11) are prepared by:

a. reacting a dihalopropanone of Formula (17) with a thiol of Formula (18) at a molar ratio of $1:\geq 2$ in an inert organic solvent such as tetrahydrofuran, ether and the like in the presence of a suitable base such as sodium hydride at a temperature of 0° to 67° C. for a period of 30 minutes to 24 hours and thereafter reducing the resultant ketone of Formula (19) with an alkali metal borohydride such as sodium borohydride at 0° C.; or b. reacting an epihalohydrin of Formula (14) with a thiol of Formula (18) at a molar ratio of 1:2 as previously described in the preparation of compounds of Formula (15); or c. reacting a 1,3-dihalo-2-propanol of Formula (20) with a thiol of Formula (18) at a molar ratio of 1:2 in an inert organic solvent such as tetrahydrofuran, ether and the like in the presence of a suitable base such as sodium hydride at a temperature of 0° to 67° C. for a period of 30 minutes to 24 hours.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

Preparation A

Epibromohydrin (2.74 g.) is added to the salt formed in situ from 4.0 g. of n-dodecyl alcohol and 880 mg. of sodium hydride (56% dispersion in mineral oil) in 120 ml. of dry tetrahydrofuran. The mixture is stirred for 1 hour at room temperature then for 4 hours at 50° C. and then evaporated to dryness. Thereafter, the residue is stirred with 7 g. of imidazole in 10 ml. dimethylformamide for 48 hours at room temperature. The resulting solution is poured into 100 ml. of water and the aqueous phase extracted with ether. The combined extracts are washed with water, dried over magnesium sulfate and evaporated. The resulting product is chromatographed on silica gel and eluted with 10% methanol in dichloromethane to yield 1-[3'-n-dodecyloxy-2'-hydroxypropyl]imidazole.

Similarly, replacing n-dodecyl alcohol in the above procedure with other appropriate alcohols or alkoxides is productive of the following 1-[3'-($R^1$-oxy)-2'-hydroxypropyl]imidazoles:

1-[3'methoxy-2'-hydroxypropyl]imidazole,
1-[3'n-butoxy-2'-hydroxypropyl]imidazole,
1-[3'-t-butoxy-2'hydroxypropyl]imidazole,
1-[3'-n-hexyloxy-2'-hydroxypropyl]imidazole,
1-[3'-n-octyloxy-2'-hydroxypropyl]imidazole,
1-[3'-n-decyloxy-2'-hydroxypropyl]imidazole, and
1-[3'-cyclohexyloxy-2'-hydroxypropyl]imidazole.

Preparation B

Epibromohydrin (2.74 g.) is added to a suspension of the salt preformed in situ from 4.2 g. of n-dodecylthiol and 880 mg. of sodium hydride (56% dispersion in mineral oil) in 100 ml. dry tetrahydrofuran. The mixture is stirred for 2 hours at room temperature and then evaporated to dryness. Thereafter, the residue is stirred with 7 g. of imidazole in 10 ml. of dimethylformamide for 48 hours at room temperature. The resulting solution is poured into 100 ml. of water and the aqueous phase extracted with ether. The combined extracts are washed well with water and then dried over magnesium sulfate and evaporated. The resulting product is chromatographed on silica gel and eluted with 10% methanol in dichloromethane to yield 1-[3'-n-dodecylthio-2'-hydroxypropyl]imidazole as an amber gum.

Similarly, replacing n-dodecylthiol in the above procedure with other appropriate thiols is productive of the following 1-[3'-($R^1$-thio)-2'-hydroxypropyl]imidazoles:

1-[3'-methylthio-2'-hydroxypropyl]imidazole,
1-[3'-isopropylthio-2'-hydroxypropyl]imidazole,
1-[3'-t-butylthio-2'-hydroxypropyl]imidazole,
1-[3'-n-hexylthio-2'-hydroxypropyl]imidazole,
1-[3'-n-heptylthio-2'-hydroxypropyl]imidazole,
1-[3'-n-octylthio-2'-hydroxypropyl]imidazole,
1-[3'-n-nonylthio-2'-hydroxypropyl]imidazole,
1-[3'-n-decylthio-2'-hydroxypropyl]imidazole, and
1-[3'-cyclohexylthio-2'-hydroxypropyl]imidazole.

Preparation C 2,3-Epoxypropyl isopropyl ether (1.16 g.) in several ml. of dry tetrahydrofuran is added to a stirred suspension formed by the addition of 50 mg. of sodium hydride (56% dispersion in mineral oil) to 2.2 8. of n-dodecylthiol in 50 ml. tetrahydrofuran. The mixture is then stirred at 60° C. After approximately 4 hours the solvent is removed from the reaction mixture and 20 ml. of water is aded to the residue. The resultant aqueous mixture is extracted with ether and the ether extracts washed with water, dried over magnesium sulfate and evaporated to yield 1-(n-dodecylthio)-3-isopropoxy-2-propanol.

Similarly, replacing 2,3-epoxypropyl isopropyl ether in the above procedure with other appropriate 2,3-epoxypropyl ethers and/or replacing n-dodecylthiol with other appropriate thiols is productive of the following 1,3-substituted-2-propanols:

1-(n-butoxy)-3-(n-dodecylthio)-2-propanol,
1-(n-octyloxy)-3-(n-octylthio)-2-propanol,
1-(n-heptylthio)-3-(n-octyloxy)-2-propanol,
1-(n-dodecyloxy)-3-(n-methylthio)-2-propanol, and
1-(cyclohexylethoxy)-3-(n-heptylthio)-2-propanol,
1-(cyclohexylthio)-3-(n-decyloxy)-2-propanol,
1-(n-butylthio)-3-(n-decyloxy)-2-propanol,
1-(n-dodecylthio)-3-(methoxy)-2-propanol,
1-(n-decylthio)-3-(n-hexyloxy)-2-propanol,
1-(t-butylthio)-3-(n-decyloxy)-2-propanol,
1-(n-dodecyloxy)-3-(methylthio)-2-propanol,
1-(n-dodecylthio)-3-(isopropoxy)-2-propanol,
1-(n-hexylthio)-3-(n-octyloxy)-2-propanol,
1-(n-butylthio)-3-(n-octyloxy)-2-propanol,
1-(ethylthio)-3-(n-octyloxy)-2-propanol,
1-(ethylthio)-3-(n-dodecyloxy)-2-propanol,
1-(n-butyloxy)-3-(n-hexylthio)-2-propanol,
1-(n-butyloxy)-3-(n-octylthio)-2-propanol,
1-(n-hexyloxy)-3-(n-hexylthio)-2-propanol and 1-(n-butylthio)-3-(n-hexyloxy)-2-propanol.

Preparation D

Epibromohydrin (6.8 g) is added with stirring to the suspension obtained by adding 2.7 g. of sodium hydride (56% dispersion in mineral oil) to 12.7 g. of cyclohexanethiol in 250 ml. of dry tetrahydrofuran. The mixture is then stirred at reflux for 6 hours, the solvent removed and 30 ml. of water is added to the residue. The resultant aqueous mixture is extracted with ether and the ether extracts washed with water, dried over magnesium sulfate and evaporated to yield 14.9 g. of 1,3-bis(-cyclohexylthio)-2-propanol as a yellow oil.

Similarly, replacing cyclohexanethiol in the above procedure with other appropriate thiols is productive of the following 1,3-bis(R¹thio)-2-propanols:

1,3-bis(n-butylthio)-2-propanol,
1,3-bis(n-pentylthio)-2-propanol,
1,3-bis(n-hexylthio)-2-propanol,
1,3-bis(n-heptylthio)-2-propanol and
1,3-bis(cyclohexylmethylthio)-2-propanol.

EXAMPLE 1

A 56% dispersion of sodium hydride in mineral oil (480 mg.) is added under nitrogen to a solution of 3.1 g. of 1-[3'-(n-dodecyloxy)-2'-hydroxypropyl]imidazole in 7 ml. dry hexamethylphosphoramide. After stirring for 1 hour at room temperature, the temperature is increased to 45° C. and stirring is continued for an additional hour. The solution is then cooled in an ice bath and 1.96 g. of 1-bromoheptane in 2 ml. of hexamethylphosphoramide is added. Thereafter, the solution is stirred for 1 hour at room temperature and then stirred for 6 hours at 55° C. The reaction mixture is poured into 100 ml. of water and the resultant aqueous mixture extracted with ether and the ether extracts washed with water. The organic phase is dried over magnesium sulfate and acidified with oxalic acid. The product which precipitates is filtered off and recrystallized from ethyl acetate to yield 1-[3'-(n-dodecyloxy)-2°-(n-heptyloxy)-propyl]imidazole oxalate.

EXAMPLE 2

Thionyl chloride (10 ml.) and 1.55 g. of 1-[3'-(n-dodecyloxy)-2'-hydroxypropyl]imidazole are warmed gently for a period of 2 hours and the solution is then evaporated to dryness. The residue is dissolved in 100 ml. of dichloromethane and rendered basic with aqueous potassium carbonate solution. The organic layer is separated, dried over magnesium sulfate and evaporated to yield 1-[2'-chloro-3'-(n-dodecyloxy)propyl]imidazole.

The chloro compound obtained above is dissolved in 10 ml. dry tetrahydrofuran and added to the salt generated in situ from 1.0 g. of n-butylthiol and 440 mg. of sodium hydride (56% dispersion in mineral oil) in 50 ml. dry tetrahydrofuran. The mixture is heated at reflux under nitrogen for 48 hours and the solvent is then removed and 30 ml. of water is added to the residue. The resultant aqueous mixture is extracted with ether and the ether extracts washed with water, dried over magnesium sulfate and evaporated to dryness. The residue is chromatographed on silica gel. Elution with 15% acetone in dichloromethane yields pure 1-[2'-(n-butylthio)-3'-n-dodecyloxy)propyl]imidazole which is taken up in ether and treated with ethereal oxalic acid yielding, after recrystallization from ethyl acetate, 1-[2'-(n-butylthio)-3'-(n-dodecyloxy)propyl]imidazole oxalate.

EXAMPLE 3

1-[3'-n-dodecylthio-2'-hydroxypropyl]imidazole (1.63 g.) in 20 ml. of dichloromethane and 2 ml. of thionyl chloride are stirred for 2 hours at room temperature. Thereafter, the reaction mixture is evaporated to dryness to yield 1-[2'-chloro-3'-(n-dodecylthio)propyl]imidazole hydrochloride as a gum.

The gun is dissolved in 10 ml. of tetrahydrofuran and the resulting solution added excess sodium methyl mercaptide (1g.) in 60 ml. of dry tetrahydrofuran.

The mixture is stirred overnight at room temperature and then evaporated to dryness. The residue is extracted with ether and the ether extract washed with water, dried over magnesium sulfate and evaporated. The residue is chromatographed on silica gel. Elution with 10% acetone in dichloromethane yields pure 1-[2'-dodecylthio)-3'-(methylthio)propyl]imidazole which is taken up in ether and treated with oxalic acid yielding, after recrystallization from ethyl acetate, 1-[2'-(n-dodecylthio)-3'-(methylthio)propyl]imidazole oxalate.

EXAMPLE 4

Crude 1-(n-dodecylthio)-3-isopropoxy-2-propanol, obtained in Preparation C, in 30 ml. of dichloromethane and 3 ml. of thionyl chloride are stirred at room temperature for 2 hours. Thereafter the solution is evaporated under reduced pressure and 3.5 g. of imidazole in 10 ml. of acetonitrile is added to the resulting residue. The reaction mixture is then stirred for 24 hours at room temperature and then stirred for 24 hours at 60° C. The solvent is then removed from the reaction mixture and 30 ml. of water is added to the resulting residue. The aqueous phase is extracted with ether and the ether extracts washed with water, dried over magnesium sulfate and acidified with oxalic acid. The product which precipitates is filtered off and recrystallized from ethyl acetate to yield 1-[2'-(n-dodecylthio)-3'-(isopropoxy)propyl]imidazole oxalate as a white solid.

EXAMPLE 5

Crude 1,3-bis(cyclohexylthio)-2-propanol, obtained in Preparation D, in 30 ml. of dichloromethane and 3 ml. of thionyl chloride are stirred at room temperature for 2 hours. Thereafter the solution is evaporated under reduced pressure and 4 g. of imidazole and 15 ml. of acetonitrile are added to the residue. The reaction mixture is stirred at 60° C. for 24 hours. Thereafter the solvent is removed and 100 ml. of water is added to the residue. The resultant aqueous phase is extracted with ether and the ether extracts washed with water, dried over magnesium sulfate and acidified with oxalic acid. The product which precipitates is filtered off and recrystallized twice from ethyl acetate to yield 880 mg. of 1-[2',3'-bis(cyclohexylthio)propyl]imidazole oxalate, m.p. 85.5°–88.5° C.

EXAMPLE 6

Repeating the procedure of Example 1 using reactants of Formulas (1) and (2) as dictated by the particular 1-[2'-($R^2$-oxy)-3'-($R^1$-oxy(thio)propyl]imidazole desired is productive of the following compounds as the oxalate salts by treatment in the conventional manner with oxalic acid:
  1-[2'-(n-dodecyloxy)-3'-(methoxy)propyl]imidazole oxalate,
  1-[3'-(t-butoxy)-2'-(n-dodecyloxy)propyl]imidazole oxalate,
  1-[3'-(cyclohexyloxy)-2'-(n-dodecyloxy)propyl]imidazole oxalate,
  1-[3'-(n-butoxy)-2'-(n-dodecyloxy)propyl]imidazole oxalate,
  1-[3'-(n-hexyloxy)-2'-(n-decyloxy)propyl]imidazole oxalate,
  1-[2',3'-bis(n-octyloxy)propyl]imidazole oxalate,
  1-[3'-(n-decyloxy)-2'-(n-hexyloxy)propyl]imidazole oxalate,
  1-[3'-(n-decyloxy)-2'-(n-heptyloxy)propyl]imidazole oxalate,
  1-[3'-(n-decyloxy)-2'-(n-octyloxy)propyl]imidazole oxalate,
  1-[2'-(cyclohexylethoxy)-3'-(n-decyloxy)propyl]imidazole oxalate,
  1-[2'-(n-butoxy)-3'-(n-dodecyloxy)propyl]imidazole oxalate,
  1-[3'-(n-dodecyloxy)-2'-(isopropoxy)propyl]imidazole oxalate,
  1-[3'-(n-dodecyloxy)-2'-(methoxy)propyl]imidazole oxalate,
  1-[2'-(n-dodecyloxy)-3'-(methylthio)propyl]imidazole oxalate,
  1-[3'-(t-butylthio)-2'-(n-dodecyloxy)propyl]imidazole oxalate,
  1-[3'-(cyclohexylthio)-2'-(n-decyloxy)propyl]imidazole oxalate, m.p. 93°–94° C.,
  1-[2'-(n-heptyloxy)-3'-(n-heptylthio)propyl]imidazole oxalate,
  1-[3'-(n-heptylthio)-2'-(n-octyloxy)propyl]imidazole oxalate,
  1-[2'-(n-octyloxy)-3'-(n-octylthio)propyl]imidazole oxalate,
  1-[2'-(cyclohexylmethoxy)-3'-(n-decylthio)propyl]imidazole oxalate,
  1-[3'-(n-dodecylthio)-2'-(methoxy)propyl]imidazole oxalate,
  1-[2'-(n-butyloxy)-3'-(n-hexylthio)propyl]imidazole oxalate,
  1-[2'-(n-hexyloxy)-3'-(n-hexylthio)propyl]imidazole oxalate,
  1-[3'-(n-hexylthio)-2'-(n-octyloxy)propyl]imidazole oxalate,
  1-[2'-(n-hexyloxy)-3'-(n-octylthio)propyl]imidazole oxalate,
  1-[2'-(n-butyloxy)-3'-(n-octylthio)propyl]imidazole oxalate,
  1-[2'-(n-butyloxy)-3'-(n-decylthio)propyl]imidazole oxalate,
  1-[2',3'-bis(n-hexyloxy)propyl]imidazole oxalate,
  1-[3'-(n-hexyloxy)-2'-(n-octyloxy)propyl]imidazole oxalate,
  1-[2'-(n-hexyloxy)-3'-(n-octyloxy)propyl]imidazole oxalate,
  1-[2'-(n-butyloxy)-3'-(n-octyloxy)propyl]imidazole oxalate.

EXAMPLE 7

Repeating the procedure of Example 3 using reactants of Formulas (6) and (8) as dictated by the particular 1-[2'-($R^2$-thio)-3'-($R^1$-thio)propyl]imidazole desired is productive of the following compounds as the oxalate salts by treatment in the conventional manner with oxalic acid:
  1-[2'-(cyclohexylthio)-3'-(methylthio)propyl]imidazole oxalate,
  1-[3'-(t-butylthio)-2'-(n-nonylthio)propyl]imidazole oxalate,
  1-[3'-(n-dodecylthio)-2'-(methylthio)propyl]imidazole oxalate, and
  1-[3'-(n-decylthio)-2'-(isopropylthio)propyl]imidazole oxalate.

EXAMPLE 8

Repeating the procedure of Example 4 using reactants of Formula (9) as dictated by the particular 1-[3'-($R^1$-oxy)-2'-($R^2$-thio)propyl]imidazole desired is productive of the following compounds as the oxalate salts by treatment in the conventional manner with oxalic acid:
  1-[3'-(n-butoxy)-2'-(n-dodecylthio)propyl]imidazole oxalate,
  1-[3'-(n-octyloxy)-2'-(n-octylthio)propyl]imidazole oxalate,
  1-[2'-(n-heptylthio)-3'-(n-octyloxy)propyl]imidazole oxalate,
  1-[3'-(n-dodecyloxy)-2'-(methylthio)propyl]imidazole oxalate,
  1-[3'-(cyclohexylethoxy)-2'-(n-heptylthio)propyl]imidazole oxalate,
  1-[2'-(cyclohexylthio)-3'-(n-decyloxy)propyl]imidazole oxalate,
  1-[2'-(n-butylthio)-3'-(n-decyloxy)propyl]imidazole oxalate,
  1-[2'-(n-dodecylthio)-3'-(methoxy)propyl]imidazole oxalate,
  1-[2'-(n-decylthio)-3'-(n-hexyloxy)propyl]imidazole oxalate,
  1-[2'-(t-butylthio)-3'-(n-decyloxy)propyl]imidazole oxalate,
  1-[3'-(n-dodecyloxy)-2'-(methylthio)propyl]imidazole oxalate, 1-[2'-(n-dodecylthio)-3'-(isopropoxy)propyl-
  ]imidazole oxalate, m.p. 90.5°-92° C.,
1-[2'-(n-hexylthio)-3'-(n-octyloxy)propyl]imidazole
  oxalate,
1-[2'-(n-butylthio)-3'-(n-octyloxy)propyl]imidazole
  oxalate,
1-[2'-(ethylthio)-3'-(n-octyloxy)propyl]imidazole oxalate,
1-[3'-(n-dodecyloxy)-2'-(ethylthio)propyl]imidazole
  oxalate,
1-[3'-(n-butyloxy)-2'-(n-hexylthio)propyl]imidazole
  oxalate,
1-[3'-(n-butyloxy)-2'-(n-octylthio)propyl]imidazole
  oxalate,
1-[3'-(n-hexyloxy)-2'-(n-hexylthio)propyl]imidazole
  oxalate and
1-[2'-(n-butylthio)-3'-(n-hexyloxy)propyl]imidazole
  oxalate.

EXAMPLE 9

Repeating the procedure of Example 5 using reactants of Formula (11) as dictated by the particular 1-[2',3'-bis(R¹-thio)propyl]imidazoles desired is productive of the following compounds as the indicated oxalate salts by treatment in the conventional manner with oxalic acid:

1-[2',3'-bis(n-hexylthio)propyl]imidazole oxalate, m.p. 88.5°-89.5° C.,
1-[2',3'-bis(n-heptylthio)propyl]imidazole oxalate, m.p. 92.5°-93.5° C.,
1-[2',3'-bis(cyclohexylmethylthio)propyl]imidazole oxalate,
1-[2',3'-bis(n-pentylthio)propyl]imidazole oxalate, m.p. 83°-84.5° C. and
1-[2',3'-bis(n-butylthio)propyl]imidazole oxalate.

EXAMPLE 10

1-[3'-(n-dodecyloxy)-2'-(n-heptyloxy)propyl-
  ]imidazole oxalate (2.3 g.) in 100 ml. of dichloromethane is shaken with excess dilute potassium carbonate solution until the salt is completely dissolved. The organic layer is then separated, washed twice with water, dried over mgnesium sulfate and evaporated to yield 1-[3'-(n-dodecyloxy)-2'-(n-heptyloxy)propyl]imidazole as a gum.

In a similar manner, the antimicrobial acid addition salts of all compounds of Formula (I) may be converted to the corresponding compounds in base form, for example 1-[2'-(n-butylthio)-3'-(n-dodecyloxy)propyl-
  ]imidazole, 1-[2'-(n-dodecylthio)-3'-(methylthio)-propyl]imidazole,
1-[2'-(n-dodecylthio)-3'-(isopropoxy)propyl-
  ]imidazole,
1-[2',3'-bis(cyclohexylthio)propyl]imidazole,
1-[2'-(n-dodecyloxy-3'-(methoxy)propyl]imidazole,
1-[3'-(t-butoxy)-2'-(n-dodecyloxy)propyl]imidazole,
1-[3'-(cyclohexyloxy)-2'-(n-dodecyloxy)propyl]-
  imidazole,
1-[3'-(n-butoxy)-2'-(n-dodecyloxy)propyl]imidazole,
1-[3'-(n-hexyloxy)-2'-(n-decyloxy)propyl]imidazole,
1-[2',3'-bis(n-octyloxy)propyl]imidazole,
1-[3'-(n-decyloxy)-2'-(n-hexyloxy)propyl]imidazole,
1-[3'-(n-decyloxy)-2'-(n-heptyloxy)propyl]imidazole,
1-[3'-(n-decyloxy)-2'-(n-octyloxy)propyl]imidazole,
1-[2'-(cyclohexylethoxy)-3'-(n-decyloxy)propyl]-
  imidazole,
1-[2'-(n-butoxy)-3'-(n-dodecyloxy)propyl]imidazole,
1-[3'-(n-dodecyloxy)-2'-(isopropoxy)propyl-
  ]imidazole,
1-[3'-(n-dodecyloxy)-2'-(methoxy)propyl]imidazole,
1-[2'-(n-dodecyloxy)-3'-(methylthio)propyl-
  ]imidazole,
1-[3'-(t-butylthio)-2'-(n-dodecyloxy)propyl-
  ]imidazole,
1-[3'-(cyclohexylthio)-2'-(n-decyloxy)propyl-
  ]imidazole,
1-[2'-(n-heptyloxy)-3'-(n-heptylthio)propyl-
  ]imidazole,
1-[3'-(n-heptylthio)-2'-(n-octyloxy)propyl]imidazole,
1-[2'-(n-octyloxy)-3'-(n-octylthio)propyl]imidazole,
1-[2'-(cyclohexylmethoxy)-3'-(n-decylthio)propyl-
  ]imidazole,
1-[3'-(n-dodecylthio)-2'-(methoxy)propyl]imidazole,
1-[2'-(n-butyloxy)-3'-(n-hexylthio)propyl]imidazole,
1-[2'-(n-hexyloxy)-3'-(n-hexylthio)propyl]imidazole,
1-[3'-(n-hexylthio)-2'-(n-octyloxy)propyl]imidazole,
1-[2'(n-hexyloxy-3'-(n-octylthio)propyl]imidazole,
1-[2'(n-butyloxy)-3'-(n-octylthio)propyl]imidazole,
1-[2'(n-butyloxy)-3'-(n-decylthio)propyl]imidazole,
1-[2',3'-bis(n-hexyloxy)propyl]imidazole,
1-[3'-(n-hexyloxy)-2'-(n-octyloxy)propyl]imidazole,
1-[2'-(n-hexyloxy)-3'-(n-octyloxy)propyl]imidazole,
1-[2'-(n-butyloxy)-3'-(n-octyloxy)propyl]imidazole,
1-[2'-(cyclohexylthio)-3'-(methylthio)propyl-
  ]imidazole,
1-[3'-(t-butylthio)-2'-(n-nonylthio)propyl]imidazole,
1-[3'-(n-dodecylthio)-2'-(methylthio)propyl-
  ]imidazole,
1-[3'-(n-decylthio)-2'-(isopropylthio)propyl-
  ]imidazole,
1-[3'-(n-butoxy)-2'-(n-dodecylthio)propyl]imidazole,
1-[3'-(n-octyloxy)-2'-(n-octylthio)propyl]imidazole,
1-[2'-(n-heptylthio)-3'-(n-octyloxy)propyl]imidazole,
1-[3'-(n-dodecyloxy)-2'-(methylthio)propyl-
  ]imidazole,
1-[3'-(cyclohexylethoxy)-2'-(n-heptylthio)propyl]-
  imidazole,
1-[2'-(cyclohexylthio)-3'-(n-decyloxy)propyl-
  ]imidazole,
1-[2'-(n-butylthio)-3'-(n-decyloxy)propyl]imidazole,
1-[2'-(n-dodecylthio)-3'-(methoxy)propyl]imidazole,
1-[2'-(n-decylthio)-3'-(n-hexyloxy)propyl]imidazole,
1-[2'-(t-butylthio)-3'-(n-decyloxy)propyl]imidazole,
1-[3'-(n-dodecyloxy-2'-(methylthio)propyl]imidazole,
1-[2'-(n-dodecylthio)-3'-(isopropoxy)propyl-
  ]imidazole,
1-[2'-(n-hexylthio)-3'-(n-octyloxy)propyl]imidazole,
1-[2'-(n-butylthio)-3'-(n-octyloxy)propyl]imidazole,
1-[2'-(ethylthio)-3'-(n-octyloxy)propyl]imidazole,
1-[3'-(n-dodecyloxy)-2'-(ethylthio)propyl]imidazole,
1-[3'-(n-butyloxy)-2'-(n-hexylthio)propyl]imidazole,
1-[3'-(n-butyloxy)-2'-(n-octylthio)propyl]imidazole,
1-[3'-(n-hexyloxy)-2'-(n-hexylthio)propyl]imidazole,
1-[2'-(n-butylthio)-3'-(n-hexyloxy)propyl]imidazole,
1-[2',3'-bis(n-hexylthio)propyl]imidazole,
1-[2',3'-bis(n-heptylthio)propyl]imidazole,
1-[2',3'-bis(cyclohexylmethylthio)propyl]imidazole,
1-[2',3'-bis(n-pentylthio)propyl]imidazole and
1-[2',3'-bis(n-butylthio)propyl]imidazole.

EXAMPLE 11

Oxalic acid is added dropwise to a stirred solution of 3,2 g. of 1-[2',3'-bis(cyclohexylthio)propyl]imidazole in 300 ml. of anhydrous ether until precipitation is complete. The product is filtered off, washed with ether, air dried and recrystallized from ethyl acetate to yield 1-[2',3'-bis(cyclohexylthio)propyl]imidazole oxalate, m.p. 85.5°–88.5° C.

In similar manner, all compounds of Formula (I) in base form can be converted to the antimicrobial acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid or p-toluenesulfonic acid.

EXAMPLE 12

The following example illustrates the preparation of representative formulations containing an active compound such as a salt of 1-[2',3'-bis(n-pentylthio)propyl]imidazole, which may be used for controlling fungi, bacteria and protozoa.

A. Topical Formulation

| | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA(butylated hydroxy anisole) | 0.01 |
| Water   qs | 100 |

All of the above ingredients, except water, are combined and heated at 60° C. with stirring. A sufficient quantity of water at 60° C. is then added with vigorous stirring to provide 100 g. of the cream formulation which is then cooled to room temperature.

B. I.V. Formulation

| | |
|---|---|
| Active compound | 0.5 g. |
| Propylene glycol | 20 g. |
| Polyethylene glycol 400 | 20 g. |
| Tween 80 | 1 g. |
| 0.9% Saline solution   qs | 100 ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

C. Oral Formulation

| | parts by weight |
|---|---|
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as a solvent. The formulation is then dried and formed into tablets (containing 200 mg. of active compound) with an appropriate tabletting machine.

What is claimed is:

1. A compound of the formula

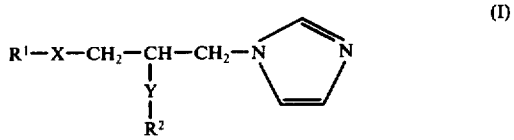

wherein $R^1$ and $R^2$ are independently alkyl having 1 to 12 carbon atoms or the group

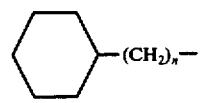

in which $n$ is 0 to 3; X and Y are independently oxygen or sulfur; and the antimicrobial acid addition salts thereof.

2. A compound of claim 1 wherein X and Y are oxygen.

3. A compound of claim 1 wherein X is sulfur and Y is oxygen.

4. A compound of claim 1 wherein X is oxygen and Y is sulfur.

5. A compound of claim 1 wherein X and Y are sulfur.

6. A compound of claim 1 wherein $R^1$ and $R^2$ are alkyl.

7. The compound of claim 6 which is 1-[2',3'-bis(n-octyloxy)propyl]imidazole and the antimicrobial acid addition salts thereof.

8. The compound of claim 6 which is 1-[3'-(n-decyloxy)-2'-(n-hexyloxy)propyl]imidazole and the antimicrobial acid addition salts thereof.

9. The compound of claim 6 which is 1-[3'-(n-decyloxy)-2'-(n-heptyloxy)propyl]imidazole and the antimicrobial acid addition salts thereof.

10. The compound of claim 6 which is 1-[3'-(n-decyloxy)-2'-(n-octyloxy)propyl]imidazole and the antimicrobial acid addition salts thereof.

11. The compound of claim 6 which is 1-[2'-(n-heptyloxy)-3'-(n-heptylthio)propyl]imidazole and the antimicrobial acid addition salts thereof.

12. The compound of claim 6 which is 1-[3'-(n-heptylthio)-2'-(n-octyloxy)propyl]imidazole and the antimicrobial acid addition salts thereof.

13. The compound of claim 6 which is 1-[2'-(n-octyloxy)-3'-(n-octylthio)propyl]imidazole and the antimicrobial acid addition salts thereof.

14. The compound of claim 6 which is 1-[2'-(n-dodecylthio)-3'-(isopropoxy)propyl]imidazole and the antimicrobial acid addition salts thereof.

15. The compound of claim 6 which is 1-[3'-(n-octyloxy)-2'-(n-octylthio)propyl]imidazole and the antimicrobial acid addition salts thereof.

16. The compound of claim 6 which is 1-[2'-(n-heptylthio)-3'-(n-octyloxy)propyl]imidazole and the antimicrobial acid addition salts thereof.

17. The compound of claim 6 which is 1-[2'-(butylthio)-3'-(n-dodecyloxy)propyl]imidazole and the antimicrobial acid addition salts thereof.

18. The compound of claim 6 which is 1-[2'-(n-dodecylthio)-3'-(methylthio)propyl]imidazole and the antimicrobial acid addition salts thereof.

19. The compound of claim 6 which is 1-[3'-(t-butyl-thio)-2'-(n-nonylthio)propyl]imidazole and the antimicrobial acid addition salts thereof.

20. The compound of claim 6 which is 1-[2',3'-bis(n-hexylthio)propyl]imidazole and the antimicrobial acid addition salts thereof.

21. The compound of claim 6 which is 1-[2',3'-bis-(n-heptylthio)propyl]imidazole and the antimicrobial acid addition salts thereof.

22. The compound of claim 6 which is 1-[2',3'-bis-(n-pentylthio)propyl]imidazole and the antimicrobial acid addition salts thereof.

23. A composition useful for inhibiting the growth of fungi, bacteria or protozoa which comprises an effective amount of a compound of the formula

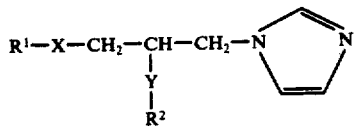
(I)

wherein $R^1$ and $R^2$ are independently alkyl having 1 to 12 carbon atoms or the group

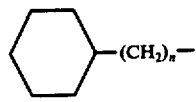

in which $n$ is 0 to 3 and X and Y are independently oxygen or sulfur; or an antimicrobial acid addition salt thereof in admixture with a suitable carrier.

24. A composition of claim 23 for pharmaceutical use wherein the carrier is a pharmaceutically acceptable, nontoxic carrier.

25. A composition of claim 24 for topical administration wherein the compound of Formula (I) is present in an amount ranging between 0.1 and 10.0 weight percent of the composition.

26. A method of inhibiting the growth of fungi, bacteria or protozoa which comprises applying to a host object containing or subject to attack by fungi, bacteria or protozoa an effective amount of a compound of the formula

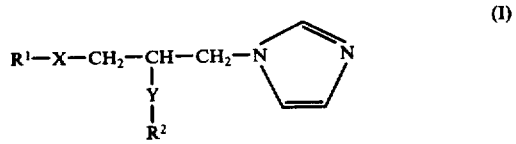
(I)

wherein $R^1$ and $R^2$ are independently alkyl having 1 to 12 carbon atoms or the group

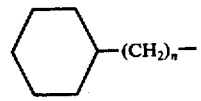

in which $n$ is 0 to 3 and X and Y are independently oxygen or sulfur; or an antimicrobial acid addition salt thereof or a composition containing same as an active ingredient.

27. The method of claim 26 wherein the compound of Formula (I) is administered topically.

28. The method of claim 26 wherein the compound of Formula (I) is administered orally or parenterally.

* * * * *